United States Patent [19]

Mouradian

[11] Patent Number: 4,503,847
[45] Date of Patent: Mar. 12, 1985

[54] PROSTHETIC NAIL

[75] Inventor: William H. Mouradian, Santa Monica, Calif.

[73] Assignee: Howmedica, Inc., New York, N.Y.

[21] Appl. No.: 339,513

[22] Filed: Jan. 15, 1982

[51] Int. Cl.³ .............................. A61F 1/04; A61F 5/04
[52] U.S. Cl. ............................... 128/92 BC; 128/92 C; 3/1.9
[58] Field of Search ............. 128/92 R, 92 B, 92 BA, 128/92 BB, 92 C, 92 D, 92 G, 92 BC

[56]           References Cited
        U.S. PATENT DOCUMENTS

| | | |
|---|---|---|
| 2,518,019 | 3/1950 | Kane . |
| 2,579,968 | 12/1951 | Rush . |
| 2,998,007 | 8/1961 | Herzog . |
| 3,025,853 | 3/1962 | Mason . |
| 3,433,220 | 3/1969 | Zickel ........................ 128/92 BA |
| 3,439,671 | 4/1969 | Kuntscher . |
| 3,441,017 | 4/1969 | Kaessmann . |
| 4,011,863 | 3/1977 | Zickel . |
| 4,055,172 | 1/1979 | Ender et al. . |
| 4,103,683 | 8/1978 | Neufeld ........................ 128/92 BC |
| 4,135,507 | 1/1979 | Harris . |
| 4,169,470 | 10/1979 | Ender et al. . |
| 4,261,351 | 3/1980 | Scherfel . |
| 4,275,717 | 6/1981 | Bolesky . |

FOREIGN PATENT DOCUMENTS 2341439  2/1975  Fed. Rep. of Germany .

OTHER PUBLICATIONS

A. Brown et al., "Internal Fixation for Supracondylar Fracture of the Femur in the Elderly Patient", The Journal of Bone and Joint Surgery, British vol. 53-B, No. 3, Aug. 1971, pp. 420-424.
Zimmer Advertisement, The Journal of Bone and Joint Surgery, vol. 37A, Jul., 1955, p. 5.
Rush Medullary Pin Advertisement, The Journal of Bone and Joint Surgery, Sep., 1960, pp. 42-43.

Primary Examiner—Richard J. Apley
Assistant Examiner—David J. Isabella
Attorney, Agent, or Firm—Pennie & Edmonds

[57]           ABSTRACT

A prosthetic nail for stabilizing fractures in a humer has an elongated slightly twisted shape and tapers substantially over its entire length from a relatively thick head to a relatively thin tip. The elevational configuration of the nail has a thin elongated generally twisted midportion with two curved ends, a larger head end and a thinner tip end. The plan configuration of the nail tapers from the head to a blunt rounded tip. Two holes for retaining screws are provided through the head end either at right angles to the elevational length of the nail or at a slight inward inclination thereto. The retaining screws have a broad shank and are threaded for retention in the bone.

23 Claims, 17 Drawing Figures

U.S. Patent    Mar. 12, 1985    Sheet 1 of 4    4,503,847
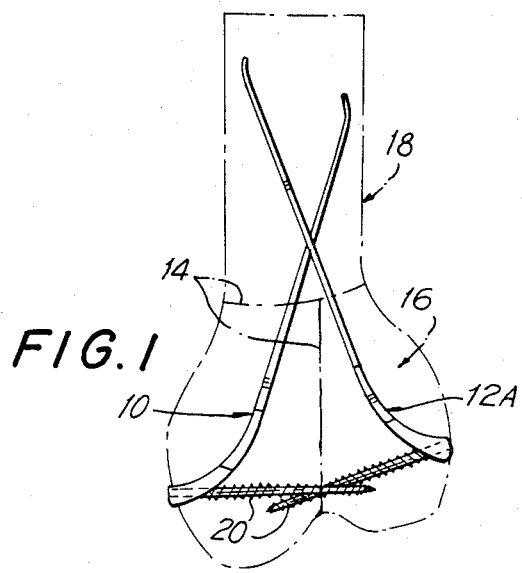
FIG.1
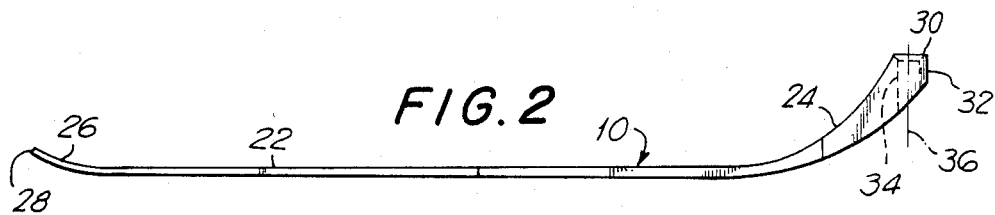
FIG.2
FIG.4
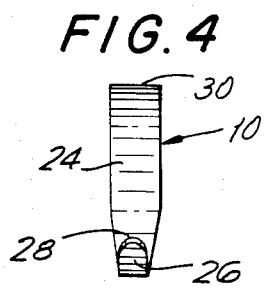
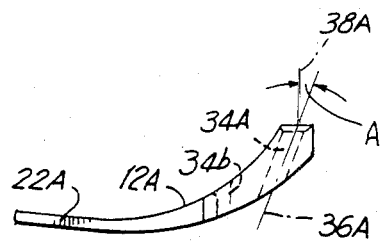
FIG.5
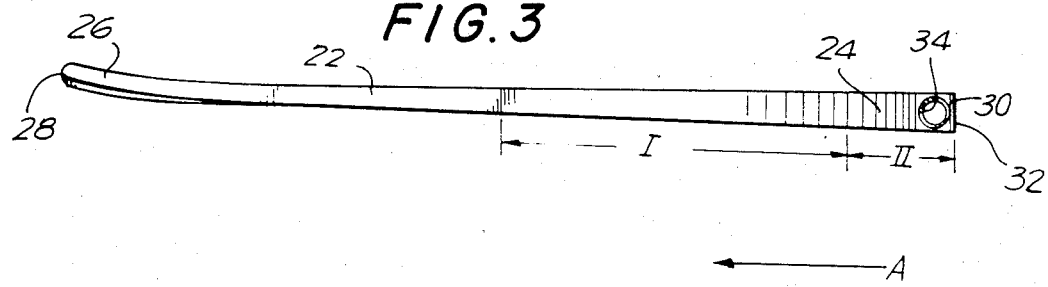
FIG.3

PROSTHETIC NAIL

TECHNICAL FIELD

The present invention relates to a prosthetic device for stabilizing fractures in bones and particularly, to an elongated prosthetic nail for stablizing fractures a region of a bone, e.g., a femur or the humerus.

BACKGROUND ART

It is well known to employ pins or nails for the purpose of attempting to stabilize certain types of fractures, for example, comminuted or complex fractures which are best treated by stabilization or internal fixation of the bone. Such pins or nails are described and illustrated in U.S. Pat. Nos. 2,579,968; 2,998,007; 3,433,220 and 3,439,671. However, the pins which are illustrated for example in the aforementioned '968 patent, although providing for connection of the broken pieces of bone, do not provide for rotational stability because of their rod-like construction. In addition, most of these known nails or pins do not provide for any securement of the same to a portion of the bone.

In an attempt to overcome the above-identified limitations of the prior art, U.S. Pat. No. 4,011,863 discloses an elongated configured prosthetic nail which is flat along the length and has two upturned end portions. However, the nail according to the '863 patent is not appropriate for use in bones where the intramedullary canal is not of a generally cylindrical nature or constant cross-section along its length. In particular, such nail cannot be satisfactorily used in the humerus bone of the human body since the humerus has a region which is varyingly elliptical in cross section at the junction of the middle and distant thirds of the humeral bone. Thus, although the nail of the '863 patent may be useful for the femur, it would not be satisfactory for use in the humerus or like bones which have an elliptical or varying elliptical configuration in cross section along the length of the bone.

DISCLOSURE OF THE INVENTION

The present invention relates to a prosthetic device for stabilizing fractures of a bone having an intramedullary canal, comprising a continuous length of biocompatible metal having a first end portion terminating in an arcurate blunt ended configuration, a second end portion configured so as to be capable of being secured to the bone, and an elongated midportion positioned between the first the second end portions, the midportion having at least a slightly twisted configuration and together with said first end portion being configured and dimensioned for insertion into the intramedullary canal of the bone.

In a preferred embodiment, the present invention relates to a prospthetic nail for stabilizing fractures of a bone having an intramedullary canal, comprising a continuous length of biocompatible metal having a first end portion terminating in a generally upturned arcurate blunt ended configuration, a second end portion being generally upturned in generally the same direction as the first end portion and being configured so as to be capable of being secured to the bone, and an elongated midportion having at least a slightly twisted configuration generally along its length and together with the first end portion being configured and dimensioned for insertion into the intramedullary canal of the bone.

The midportion is generally tapered in width along its length from the second end portion toward the first end portion. Also the midportion preferably is generally tapered in its thickness along its length from said second end portion toward said first end portion. Also the nail is generally tapered in its thickness along its length from the second end portion toward the first end portion. In addition, the second end portion is of a generally constant width and is of a generally squared-off configuration at its topmost upturned portion. The sides of the second end portion are generally parallel to each other. The first end portion is also of a generally constant width and the first end portion substantially continues the thickness of the thinner portion of said midportion.

In order to permit securement of the nail to the bone, the second end portion includes one or two holes configured and dimensioned for receiving means such as retaining screws for securing the second end portion to the bone. Preferably the holes are parallel and are disposed generally transverse to said midportion.

In a second preferred embodiment of the present invention, a prosthetic nail comprising an elongated length of biocompatible metal having plan and elevational configurations, the plan configuration tapering from a relatively larger head to a rounded blunt tip, the elevational configuration having a relatively thin tapered elongated midportion and arcuate head and tip ends extending on the same side of said midportion, the midportion having at least a slightly twisted configuration generally along its length, the arcuate head end having ample inner and outer radii providing a thickness at the extremity similar to that of the plan head configuration, the arcuate tip end of the elevational configuration having relatively smaller radii smoothly continuing the smaller end of the midportion a short distance, and at least one hole for a retaining screw through the end of the head being disposed substantially at right angles to the midportion in the elevational configuration. The retaining screw hole has an axis disposed at right angles to the midportion of the nail in elevational configuration. In an alternative embodiment, the screw hole axis is disposed at slightly less than right angles to said midportion of the nail in elevational configuration. The plan configuration has a tapered midportion and substantially parallel sided head and tip sections connected thereto, and the tapered midportion has a ratio of taper of about two to one from wider to narrower ends. The midportion in elevational configuration substantially continues the thickness of the thinner portion of the midportion. The head end in elevational configuration is squared off at its top and terminal sides about the retaining screw hole.

BRIEF DESCRIPTION OF THE DRAWINGS

The present invention is described in detail below herein with reference to the drawings in which:

FIG. 1 is a schematic view in elevation of a pair of prosthetic nails of a construction according to the present invention so as to stabilize the fracture of a bone.

FIG. 2 is an elevational longitudinal view of one of the prosthetic nails shown in FIG. 1.

FIG. 3 is a top plan longitudinal view of the prosthetic nail shown in FIG. 2.

FIG. 4 is a left end elevational view of the prosthetic nail shown in FIG. 2.

FIG. 5 is a partial top plan longitudinal view of an alternative embodiment of the supracondylar prosthetic nail shown in FIG. 2 illustrating two retaining screw holes.

DESCRIPTION OF THE BEST MODE FOR CARRYING OUT THE INVENTION

Figure 3A:
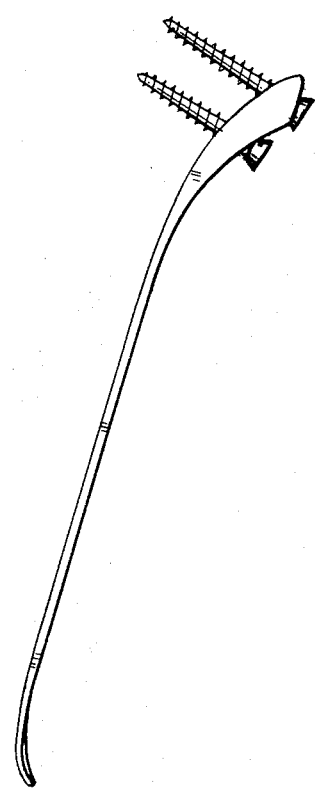
FIG. 3a is a side longitudinal view of a prosthetic nail according to the present invention illustrating two retaining screws inserted therethrough.

In the description which follows, any reference to either orientation or direction is intended primarily for the purpose of illustration and is not intended in any way as a limitation of the scope of the present invention. Referring to the drawings, a pair of prosthethic nails 10 and 12A according to the present invention are shown in FIG. 1 for securing a T-shaped fracture designated by phantom lines 14 in a region 16 of a bone 18 such as the humerus, which is partially shown in FIG. 1. Retaining screws 20 secure the head of nails 10 and 12A to the area of humerus 18 and secure the split portions of humerus 18 together. Nails 10 and 12 are inserted with their longer ends disposed within the intramedullary canal (not shown) of humerus 18.

Prosthetic nails 10 and 12A may be used for stabilizing various types of fractures of a region of the humerus either singly or in pairs. Nails 10 and 12A and retaining screws 20 are made of a biocompatible metal such as stainless steel which is known under the tradename LVM 316. If desired, other suitable material, e.g., Vitallium may be used. Vitallium is the trademark of Howmedica, Inc., for a special cobalt-chromium alloy developed and used for cast partial and full dentures and for internal applications by surgeons. Cobalt and chromium constitute over 90% of its composition. Vitallium is characterized by a specific gravity of 8.29; tensile strength, 95,000 lb./sq. in. minimum; 2% offset yield strength, 65,000 lb./sq. in. minimum; reduction of area, 8% minimum, elongation 8% lb./sq. in. When polished it is exceedingly smooth and permanently lustrous. Its outstanding qualities are clinical inertness in relation to living tissues and high degree of resistance to corrosion. Use of such biocompatible materials permits the prosthetic nail to be implanted in a human body without any adverse effects.

Referring to FIGS. 2 and 3, a nail 10 is shown in a side elevational and top plan view, respectively. Also an end configuration is shown in FIG. 4. The nail 10 has a substantially twisted or helically shaped thin midportion 22 disposed between a second end portion, i.e., an upwardly curved head end 24 and a first end portion, i.e., upwardly curved tip end 26. The purpose of the twist will be explained in more detail below. Midportion 22 also preferably tapers from a maximum thickness at the head end 24 to a minimum thickness at the tip end 26. The head end 24 is formed for example by an inner and outer radii which are different in dimension. The curved head portion 24 extends longitudinally from the twisted midportion 22. The curved tip end 26 extends longitudinally from the outer end of twisted midportion 22 and has parallel outer and inner radii, e.g., forming an arc of about 30°.

Referring to FIG. 3, the nail 10 has a tapered intermediate portion I extending from the head end 24 from a distance H inside from the head of nail 10. The rest of the plan configuration of nail 10 has parallel sides. Plan tip 28 has a rounded blunt end of full radius.

Head end 24 as shown in FIG. 2 has square top and side ends, 30 and 32, which contain hole 34 for receiving retaining screw 20. Hole 34 has its axis 36 disposed substantially perpendicular to the length of nail 10. This is described as a lateral configuration for retaining screw 20. FIG. 5 shows what is described as a medial disposition for lag screw 20 by inclination of its axis 36A in a direction toward the first end position at an angle A of about 15° relative to a perpendicular line 38A to the length of nail 12A. FIG. 5 also shows an alternative embodiment having two retaining screws 34A and 34B. Retaining screw holes 34, 34A and 34B have upper counter-sunk ends.

Figure 10:

The retaining screws 20 may vary in length, as desired. Each screw 20 has a tapered flat head with a hexagonal socket. The tip is pointed and has V-shaped self-tapping threads for firm bone engagement. In addition, the screw 20 has a broad shank as illustrated in FIG. 10 of a six page Howmedica bulletin entitled "Howmedica Surgical Techniques: The Mouradian Humeral Fixation Device Surgical Technique" (hereinafter the "Howmedica bulletin"). This Howmedica bulletin is incorporated herein and is presented hereinbelow in its entirety.

The twisted configuration of nails 10 and 12A allows them to be used in the humerus whose shaft becomes elliptical by the junction of the middle and distal thirds and helps prevent rotational displacement of the implanted nail. The gentle taper over substantially the entire length of the nails provides variable resistance to bending in different portions of its length in a manner similar to that obtained by a varying layer spring. The blunt dull tip end prevents the wall of the intramedullary canal from being pierced. Nails 10 and 12A are intended for use in stabilizing fractures in the proximal one-third area of the humerus, for repairing various types of fractures such as T-shaped, condylar or any other fracture therein.

The nail 10 shown in FIG. 3 has a clockwise twist as seen in the direction of the arrow "A". This nail 10 is preferred for the right humerus which has an intramedullary canal which twists clockwise in the direction from the shoulder to to the elbow. If desired, a pair of nails, one having a clockwise twist and the other having a counterclockwise twist can be used simultaneously in any given humerus. In such case, the pair of nails are accordingly inserted in the greater and the lesser tuberosities, with the insertion in the former being directed to the lateral condyle and the latter to the medial condyle. The use and insertion of the prosthetic nails are described in even greater detail in the Howmedica bulletin whose comments have been incorporated here in their entirety.

Thus, the prosthetic nails according to the present invention provide not only for greater rotational and bending stability but also as well for proximal and distal fixation.

The surgical technique for employing the prosthetic device of the subject invention is set forth below as presented in the aforementioned Howmedica bulletin.

I claim:

1. A prosthetic device for stabilizing fractures of a bone having an intramedullary canal which is not constant in cross-section along its length, comprising a continuous length of biocompatible metal having a first end portion terminating in an arcuate blunt ended configuration, a second end portion configured so as to be capable of being secured to the bone, and an elongated midportion positioned between said first and said second end portions, said midportion having a predetermined and preformed twisted configuration and together with said first end portion being configured and dimensioned for insertion into the intramedullary canal of the bone, said twisted configuration allowing for use in a bone having an intramedullary canal which is not constant in cross-section along its length so as to prevent rotational displacement of the nail.

2. A prosthetic nail for stabilizing fractures of a bone having an intramedullary canal which is not constant in cross-section along its length, comprising a continuous length of biocompatible metal having a first end portion terminating in a generally upturned arcurate blunt ended configuration, a second end portion being generally upturned in generally the same direction as said first end portion and being configured so as to be capable of being secured to the bone, and an elongated midportion having a predetermined and preformed twisted configuration generally along its length and together with said first end portion being configured and dimensioned for insertion into the intramedullary canal of the bone, said twisted configuration allowing for use in a bone having an intramedullary canal which is not constant in cross-section along its length so as to prevent rotational displacement of the nail.

3. The prosthetic nail according to claim 2 wherein said midportion is generally tapered in width along its length from said second end portion toward said first end portion.

4. The prosthetic nail according to claim 3 wherein said midportion is generally tapered in its thickness along its length from said second end portion toward said first end portion.

5. The prosthetic nail according to claim 3 being generally tapered in its thickness along its length from said second end portion toward said first end portion.

6. The prosthetic nail according to claim 5 wherein said second end portion is of a generally constant width.

7. The prosthetic nail according to claim 6 wherein said second end portion is of a generally squared off configuration at its topmost upturned position.

8. The prosthetic nail according to claim 7 wherein said second end portion has sides which are generally parallel to each other.

9. The prosthetic nail according to either of claims 6 or 8 wherein said first end portion is of a generally constant width.

10. The prosthetic nail according to claim 9 wherein said midportion has a ratio of tape of approximately two to one in the direction from said second end portion to said first end portion.

11. The prosthetic nail according to claim 10 wherein said first end portion substantially continues the thickness of the thinner portion of said midportion.

12. The prosthetic nail according to claim 11 wherein said second end portion includes at least a first hole configured and dimensioned for receiving a first means for securing said second end portion to the bone.

13. The prosthetic nail according to claim 12 wherein said at least one hole is disposed generally transverse to said midportion.

14. The prosthetic nail according to claim 12 further including a second hole for receiving a second means for additionally securing said second end portion to the bone.

15. The prosthetic nail according to claim 14 wherein said first end said second holes are disposed so that their respective axes are generally parallel to each other.

16. The prosthetic nail according to claim 15 wherein said at least one hole extends through said topmost upturned portion of said second end portion.

17. A prosthetic nail for stabilizing fractures of a humerus having an intramedullary canal which is not of constant cross-section along its length, comprising a continuous length of biocompatible metal having a first end portion terminating in a generally upturned arcuate blunt ended configuration, a second end portion being generally upturned in generally the same direction as said first end portion and being configured so as to be capable of being secured to the humerus, and an elongated midportion having a predetermined and preformed twisted configuration generally along its length and together with said first end portion being configured and dimensioned for insertion into the intramedullary canal of the humerus so as to prevent rotational displacement of the nail.

18. A prosthetic nail comprising an elongated length of biocompatible metal having plan and elevational configurations, the plan configuration tapering from a relatively larger head to a rounded blunt tip, the elevational configuration having a relatively thin tapered elongated midportion and arcuate head and tip ends extending on the same side of said midportion, said midportion having a predetermined and preformed twisted configuration generally along its length, the arcuate head end having ample inner and outer radii providing a thickness at the extremity similar to that of the plan head configuration, the arcuate tip end of the elevational configuration having relatively smaller radii smoothly continuing the smaller end of said midportion a short distance, and at least one hole for a retaining screw through the end of said head being disposed substantially at right angles to said midportion in the elevational configuration, said twisted configuration allowing for use in a bone having an intramedullary canal which is not constant in cross-section along its length so as to prevent rotational displacement of the nail.

19. The prosthetic nail according to claim 18 wherein the retaining screw hole has an axis, and the axis is disposed at right angles to said midportion of the nail in elevational configuration.

20. The prosthetic nail according to claim 18 wherein the retaining screw hole has an axis, and the axis is disposed at slightly less than right angles to said midportion of the nail in elevational configuration.

21. The prosthetic nail according to claim 18 wherein the plan configuration has a tapered midportion and substantially parallel sided head and tip sections connected thereto, and the tapered midportion has a ratio of taper of about two to one from wider to narrower ends.

22. The prosthetic nail according to claim 18 wherein said midportion in elevational configuration substantially continues the thickness of the thinner portion of said midportion.

23. The prosthetic nail according to claim 18 wherein said head end in elevational configuration is squared off at its top and terminal sides about the retaining screw hole.

* * * * *

UNITED STATES PATENT AND TRADEMARK OFFICE
CERTIFICATE OF CORRECTION

PATENT NO. : 4,503,847

DATED : March 12, 1985

INVENTOR(S) : WILLIAM H. MOURADIAN

It is certified that error appears in the above-identified patent and that said Letters Patent is hereby corrected as shown below:

Column 4, between lines 60 and 61, the following should be inserted:

--<u>Rationale</u>

The function of the Mouradian Humeral Fixation Device is based on several observations. Functionally and structurally the proximal humerus can be divided into three parts: The head, the region of the tuberosities, and the shaft. Inspection of both anatomic and surgical specimens reveals that the head usually contains abundant cancellous bone, even in osteoporotic patients. Distally the shaft is comprised of dense cortical bone, becoming elliptical by the junction of the middle and distal thirds. The region of the tuberosities represents a zone of transition, being frequently deficient in both cortical and cancellous bone.

UNITED STATES PATENT AND TRADEMARK OFFICE
CERTIFICATE OF CORRECTION

PATENT NO. : 4,503,847
DATED : March 12, 1985
INVENTOR(S) : WILLIAM H. MOURADIAN It is certified that error appears in the above—identified patent and that said Letters Patent is hereby corrected as shown below:

Fractures frequently involve comminution and loss of substance in the region of the tuberosities and surgical neck, precisely where the canal is most capacious and deficient in both cancellous and cortical bone. This suggests that this are be termed a "no man's land" of fracture fixation.

Thus, the primary requirement for a fixation device in this region is to join the head, with its cancellous bone stock, to the shaft, with its cortical bone stock. Furthermore, the device should not depend heavily on fixation in the region of the tuberosities.

Functional Design

The humeral rod and fixation screw function as follows: A broad, flanged rod provides intramedullary

UNITED STATES PATENT AND TRADEMARK OFFICE
CERTIFICATE OF CORRECTION

PATENT NO. : 4,503,847      Page 3 of 22
DATED : March 12, 1985
INVENTOR(S) : WILLIAM H. MOURADIAN It is certified that error appears in the above—identified patent and that said Letters Patent is hereby corrected as shown below:

fixation distally with greater rotational stability than can be obtained with standard intramedullary devices. Proximally, cancellous screws are placed in the head, through the nail tunnels, which control screw angulation.

In summary, this device combines several important features: Cancellous screw fixation occurs proximally in the head, even in the presence of tuberosity comminution. Distally, intramedullary fixation provides greater rotational stability and three point fixation, without reaming or extensive shaft exposure.

Indications

When surgery is indicated in traumatic and atraumatic fractures and lesions of the shoulder and

UNITED STATES PATENT AND TRADEMARK OFFICE
CERTIFICATE OF CORRECTION

PATENT NO. : 4,503,847
DATED : March 12, 1985
INVENTOR(S) : WILLIAM H. MOURADIAN It is certified that error appears in the above—identified patent and that said Letters Patent is hereby corrected as shown below:

proximal third of the humerus, including two-and three-part fractures and fracture/dislocations. In four-part fractures and fracture/dislocations, the device is indicated in healthy individuals with a reasonable life expectancy.

Contraindications

Intra-articular fractures and isloated fractures of the anatomic neck may require different fixation. Deficiency of the humeral shaft may preclude insertion of the device.

Operative Technique

Preparation

Image intensification is recommended. Pre-op

UNITED STATES PATENT AND TRADEMARK OFFICE
CERTIFICATE OF CORRECTION

PATENT NO. : 4,503,847
DATED : March 12, 1985
INVENTOR(S) : WILLIAM H. MOURADIAN It is certified that error appears in the above—identified patent and that said Letters Patent is hereby corrected as shown below:

films of the humerus are advised in very small patients to check length. Prep and drape with arm and shoulder free. The image intensifier C-arm is positioned to come from the opposite side of the table.

Closed Rodding

Figure 6:
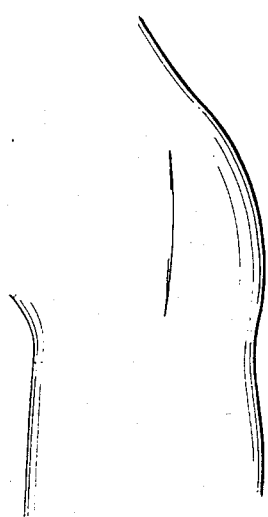

Most closed roddings are best accomplished utilizing one fixation screw. A lateral deltoid splitting incision is made with care to avoid the axillary nerve (Figure 6). The deltoid muscle may be detached on each side in a "T" fashion to increase exposure. The greater tuberosity is located by palpation. The anterior inferior portion of the tuberosity is used for insertion, locating the anterior border by palpation of the bicipital groove. If substantial supraspinatis insertion is present, it is

UNITED STATES PATENT AND TRADEMARK OFFICE
CERTIFICATE OF CORRECTION

Figure 7:
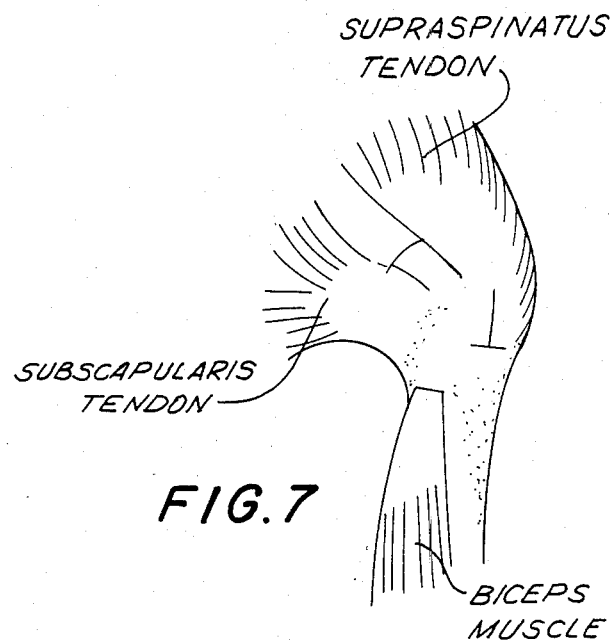
FIGS. 6-16 are illustrations indicating a surgical technique for employing the prosthetic nail of the present invention.

PATENT NO. : 4,503,847
DATED : March 12, 1985
INVENTOR(S) : WILLIAM H. MOURADIAN It is certified that error appears in the above—identified patent and that said Letters Patent is hereby corrected as shown below:

incised in the direction of its fibers and meticulously elevated (Figure 7).

Figure 8:
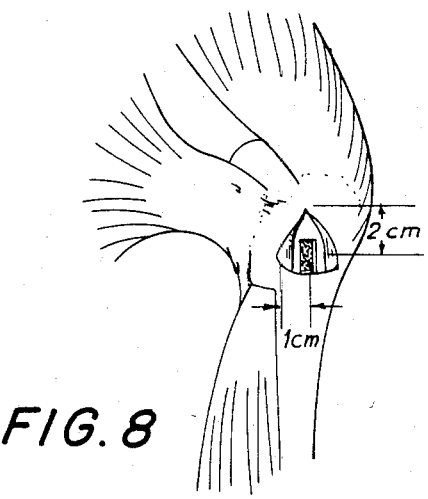
Figure 9:
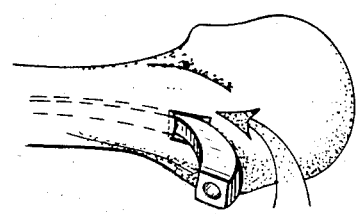

Drill a hole 1/4" in diameter at a point 2cm distal to the superior border of the tuberosity and 1cm medial to the bicipital groove, confirming position by image intensification. Enlarge the hole to a rectangular shape approximately 1.0cm in width x 1.5cm in length (Figure 8). A longer entry port may be required if two screws are used. The rod can now be inserted (Figure 9). (See rod insertion.)

Open Rodding

A delto-pectoral splitting incision is made (Figure 10). Meticulous detachment of the anterior deltoid is accomplished using a scalpel and a sharp

UNITED STATES PATENT AND TRADEMARK OFFICE
CERTIFICATE OF CORRECTION

PATENT NO. : 4,503,847

DATED : March 12, 1985

INVENTOR(S) : WILLIAM H. MOURADIAN

It is certified that error appears in the above—identified patent and that said Letters Patent is hereby corrected as shown below:

periosteal elevator, preserving adequate periosteum on the reflected deltoid for reattachment. Resect the coracoacromial ligament or perform an acromioplasty as described by Neer* to aid in operative exposure and help reduce post-operative impingement.

Often the joint capsule is found to be torn and the biceps tendon visible. If not, locate the groove by palpation, avoiding unnecessary dissection, as vascular supply to the head may be compromised. The biceps tendon serves as an important landmark, and it should be located

---

\* Neer, C.S., II, Displaced Proximal Humeral Fractures Part 1. Classification and Evaluation, J. Bone and Joint Surg. 52-A: 1077-1089, Sept. 1970.
Neer, C.S., II, Displaced Proximal Humeral Fractures, Part II. Treatement of Three-Part and Four-Part Displacement, J. Bone and Joint Surg., 52-A: 1090-1103, Sept. 1970

UNITED STATES PATENT AND TRADEMARK OFFICE
CERTIFICATE OF CORRECTION

PATENT NO. : 4,503,847  Page 8 of 22
DATED : March 12, 1985
INVENTOR(S) : WILLIAM H. MOURADIAN It is certified that error appears in the above—identified patent and that said Letters Patent is hereby corrected as shown below:

and tagged with umbilical tapes for orientation. Often, it is helpful to divide the tendon proximally, tagging it distally for later use of a soft tissue graft. In irreducible cases, the biceps tendon or the muscle itself is often found in the fracture site.

The sequence of events at this point is often determined by the nature of the dislocation and the severity of the fracture. Reduction of the subcoracoid dislocation is best deferred until adequate control of the tuberosities is gained. In some three-and four-part dislocations the head fragment is impacted centrally between the tuberosity fragments in varying positions. Gentle manipulative reduction at this point, prying carefully with a finger or blunt instrument, may successfully reduce the head. This is desirable and

UNITED STATES PATENT AND TRADEMARK OFFICE
CERTIFICATE OF CORRECTION

PATENT NO. : 4,503,847                      Page 9 of 22
DATED : March 12, 1985
INVENTOR(S) : WILLIAM H. MOURADIAN It is certified that error appears in the above—identified patent and that said Letters Patent is hereby corrected as shown below:

usually facilitates reduction of the tuberosities, with everything falling into place after reduction of the head. In the most severe and delayed cases, however, displacement and comminution are too severe, necessitating mobilization and control of the subcapularis and supraspinatus before reduction can be accomplished.

In either case, the supraspinatus tendon and its greater tuberosity fragments are delivered into the field, using the index finger for blunt extracapsular dissection. The tendon is controlled with a clamp. Multiple horizontal mattress sutures of #1 resorbable synthetic sutures are placed through the tendon and bony fragments. These are double armed, and clampled for later use. Control of the lesser tuberosity is gained in the same fashion with multiple sutures, bearing in mind that

UNITED STATES PATENT AND TRADEMARK OFFICE
CERTIFICATE OF CORRECTION

PATENT NO. : 4,503,847

DATED : March 12, 1985

INVENTOR(S) : WILLIAM H. MOURADIAN

It is certified that error appears in the above—identified patent and that said Letters Patent is hereby corrected as shown below:

reconstitution of the tuberosities will depend on these sutures. A dislocated head can now be reduced, using extreme care to avoid unnecessary dissection. Expose the distal fracture site. Anatomic reduction is severely comminuted cases is frequently made impossible by loss of substance and care must be taken to restore as much stability as possible.

Rod Insertion

Figure 11:
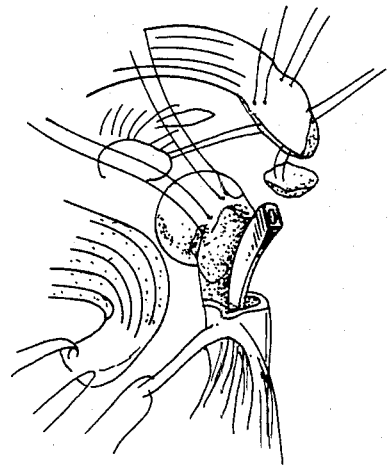

The rod may be inserted through any entry port in the greater tuberosity as noted, or directly into the fracture site in comminuted cases (Figure 11).

In any given case the preferred entry route is a matter of surgical judgment and depends on several factors: In simple cases, entry through the tuberosity is

UNITED STATES PATENT AND TRADEMARK OFFICE
CERTIFICATE OF CORRECTION

PATENT NO. : 4,503,847

DATED : March 12, 1985

INVENTOR(S) : WILLIAM H. MOURADIAN

Figure 12:
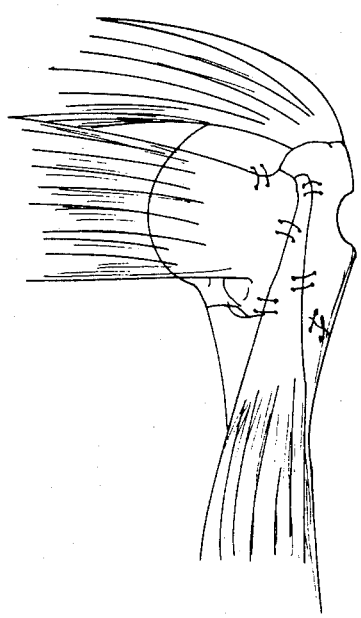

It is certified that error appears in the above-identified patent and that said Letters Patent is hereby corrected as shown below:

preferred. In three-and four-part fractures and fracture/dislocations if the tuberosity is reasonably intact and loss of substance has not been severe, then entry through the tuberosity is also preferred. This will facilitate the most anatomic reduction. With marked tuberosity comminution or loss of substance, entry directly through the fracture site is necessary. If entry is to be accomplished through an intact tuberosity, suture the fragments together and then proceed as in a closesd rodding (Figure 12). Two screw fixation is recommended. The configuration of the distal canal usually guides the rod into retroversion as it is inserted. When fully inserted, the tunnel should point in about $35°$ of retroversion, which may be estimated by flexing the elbow

UNITED STATES PATENT AND TRADEMARK OFFICE
CERTIFICATE OF CORRECTION

Figure 13:
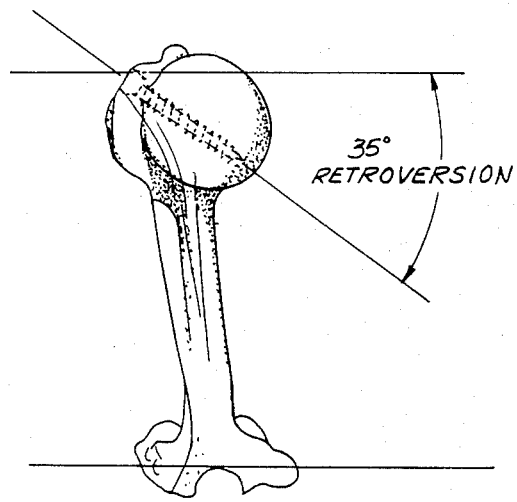

PATENT NO. : 4,503,847  Page 12 of 22
DATED : March 12, 1985
INVENTOR(S) : WILLIAM H. MOURADIAN It is certified that error appears in the above—identified patent and that said Letters Patent is hereby corrected as shown below:

and pointing the forearm toward the ceiling. Rod retroversion is downward from the horizontal in this position (Figure 13).

With significant loss of substance, it may be difficult to insert the rod distally enough into the shaft through the fracture site. It may be necessary to remove a portion of the lateral cortex, creating a small window to allow for adequate insertion. Adequate distal insertion is necessary to allow for proper impaction of the head against the shaft. The rod may be tapped gently into place, but excessive force should be avoided. Image intensification confirms reduction and insures that adequate impaction of the fragments is possible. This should be done prior to screw insertion. If inserted through a port in the greater tuberosity, the rod is

UNITED STATES PATENT AND TRADEMARK OFFICE
CERTIFICATE OF CORRECTION

PATENT NO. : 4,503,847
DATED : March 12, 1985
INVENTOR(S) : WILLIAM H. MOURADIAN It is certified that error appears in the above—identified patent and that said Letters Patent is hereby corrected as shown below:

driven distally enough so that the supraspinatus may be sewn together over it.

Screw Insertion

Insert a small K-wire through the rod tunnel deep into the cancellous bone of the head, confirming the position with image intensification. Select the appropriate length screw. Pre-drill using a 4.5cm drill bit.

Cross screw position is important. If one screw is to be used, a low center positioning is desirable. Two screws are preferred in more complex fractures. The top screw should be about two-thirds of the way up.

During insertion the contralateral index finger may be placed on the glenoid labrum to aid in orientation

UNITED STATES PATENT AND TRADEMARK OFFICE
CERTIFICATE OF CORRECTION

Figure 14:
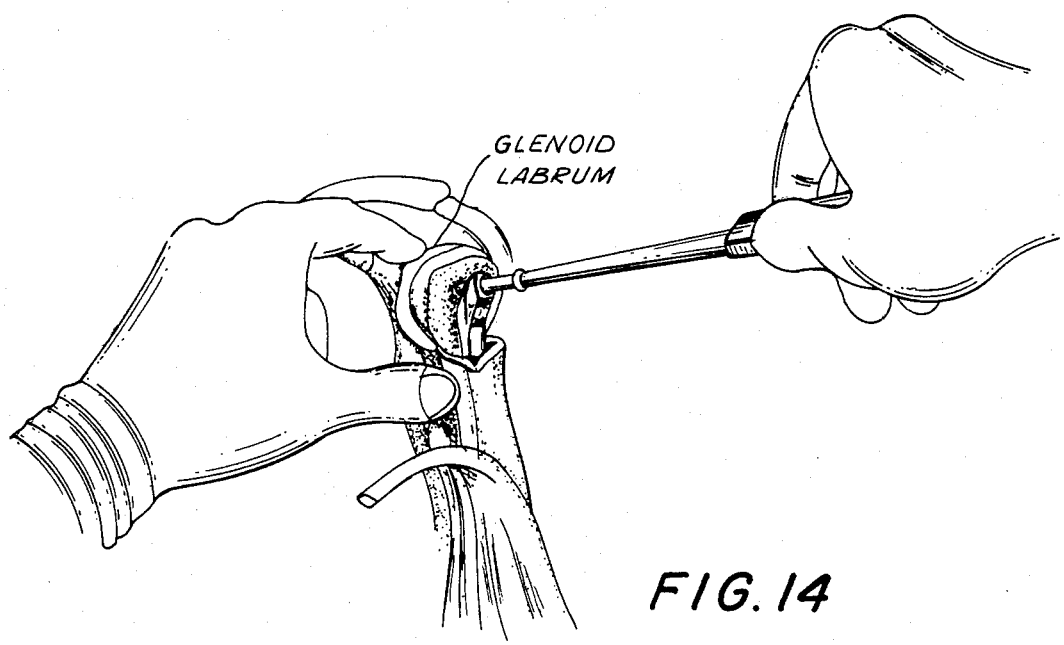

PATENT NO. : 4,503,847
DATED : March 12, 1985
INVENTOR(S) : WILLIAM H. MOURADIAN It is certified that error appears in the above—identified patent and that said Letters Patent is hereby corrected as shown below:

(Figure 14). Image intensification is particularly helpful at this juncture, especially in blind roddings. Tighten until flush, using "two-finger" technique to avoid overtightening. Confirm position with imge intensification. The screw tip should come to within 2mm of the cortex. There should be adequate impaction of the head against the neck.

Figure 15:
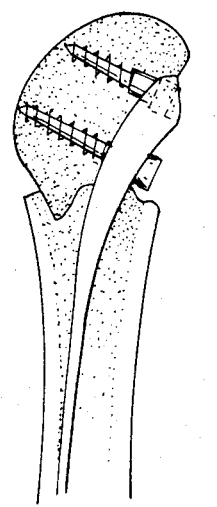

Since anatomic reduction is frequently impossible in comminuted fractures, some degree of shortening, medial displacement of the shaft, and valgus displacement of the head will frequently have to be accepted to restore stability (Figure 15). Reconstitute

UNITED STATES PATENT AND TRADEMARK OFFICE
CERTIFICATE OF CORRECTION

PATENT NO. : 4,503,847
DATED : March 12, 1985
INVENTOR(S) : WILLIAM H. MOURADIAN It is certified that error appears in the above—identified patent and that said Letters Patent is hereby corrected as shown below:

the tuberosities according to the technique of Neer.*

Figure 16:
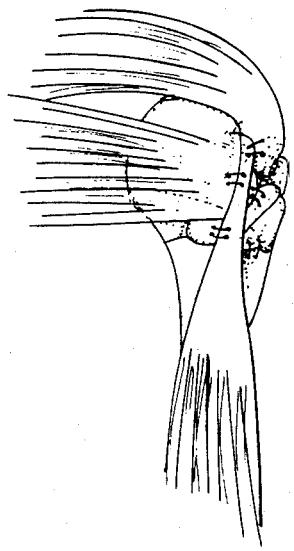

Begin from medial to lateral, attaching the multiple sutures of the lessertuberosity and subscapularis to the anterior joint capsule. The biceps tendon is retrieved from distally and sewn into place as a soft tissue suture and graft. Cancellous bone graft may be added at this juncture to restore volume to the head. The supraspinatus and remnants of the greater tuberosity are attached to the capsule, the biceps tendon, and subscapularis (Figure 16).

---

* Neer, C.S., II, Displaced Proximal Humeral Fractures, Part 1. Classification and Evaluation, J. Bone and Joint Surg. 52-A 1077-1089, Sept. 1970
Neer, C.S., II, Displaced Proximal Humeral Fractures Part II II. Treatment of Three-Part and Four-Part Deplacement, J. Bone and Joint Surg. 52-A 1090-1103, Sept. 1970.

UNITED STATES PATENT AND TRADEMARK OFFICE
CERTIFICATE OF CORRECTION

PATENT NO. : 4,503,847
DATED : March 12, 1985
INVENTOR(S) : WILLIAM H. MOURADIAN It is certified that error appears in the above—identified patent and that said Letters Patent is hereby corrected as shown below:

Post-Operative Care

A shoulder immobilizer offering substantial protection is used. In less comminuted cases with good stability "rock-a-bye baby" exercises are begun in the first post-operative week. Gentle mobilization of the elbow is begun. In severally comminuted cases, avoid mobilization until after the second or third post-operative week. At this time pendulum exercises are begun. The patient is progressed according to individual tolerance and need. In complex cases a lengthy period of intensive rehabilitation may be needed.

Surgical Tips To Help Avoid Problems

Certain problems have been noted to occur with surgeons not experienced with the technique. The most

UNITED STATES PATENT AND TRADEMARK OFFICE
CERTIFICATE OF CORRECTION

PATENT NO. : 4,503,847
DATED : March 12, 1985
INVENTOR(S) : WILLIAM H. MOURADIAN It is certified that error appears in the above—identified patent and that said Letters Patent is hereby corrected as shown below:

common recurrent problems are as follows:

1. Complex cases are often hampered by inadequate exposure. Do not hesitate to extend the deltopectorial skin incision laterally along the top of the clavicle and acromion. Use sharp instruments. Meticulous subperiosteal elevation of the deltoid begins superiorly along the midline of the clavicle. Continue anteriorly over the ridge, raising a generous flap of periosteum. This will preserve adequate periosteum on the reflected deltoid for reattachment to the abundant superior clavicular periosteum. Avoid electrocautery.

UNITED STATES PATENT AND TRADEMARK OFFICE
CERTIFICATE OF CORRECTION

PATENT NO. : 4,503,847
DATED : March 12, 1985
INVENTOR(S) : WILLIAM H. MOURADIAN It is certified that error appears in the above—identified patent and that said Letters Patent is hereby corrected as shown below:

2. It is important to follow the proper sequence in reducing the fracture fragments. In three-and four-part fracture dislocations, careful assessment of the anatomy is necessary to determine if reduction of the head should be attempted before or after mobilization and control of the tuberosities. Generally an early attempt at reduction is indicated. One should not persist if this is not accomplished easily.

3. Restoration of stability is important in preventing loss of reduction postoperatively. In comminuted cases, a

UNITED STATES PATENT AND TRADEMARK OFFICE
CERTIFICATE OF CORRECTION

PATENT NO. : 4,503,847

DATED : March 12, 1985

INVENTOR(S) : WILLIAM H. MOURADIAN

It is certified that error appears in the above—identified patent and that said Letters Patent is hereby corrected as shown below:

useful although uncommon approach is to consider the proximal humerous as biomechanically similar to the femur. The medial cortex is thus analogous to the calcar femorale and may be accordingly considered to be the calcar humerale. Anatomic reduction is frequently impossible due to the loss of substance. Subsequent displacement into varus is common. This can result not only in the appliance cutting out superiorly, but also in late subacromial impingement. Thus when reducing the fracture, reconstitution of this medial buttress is important. This can be facilitated, the tendency to

UNITED STATES PATENT AND TRADEMARK OFFICE
CERTIFICATE OF CORRECTION

PATENT NO. : 4,503,847

DATED : March 12, 1985

INVENTOR(S) : WILLIAM H. MOURADIAN

It is certified that error appears in the above–identified patent and that said Letters Patent are hereby corrected as shown below:

varus deformity minimized by the following: The fracture should be reduced in valgus. Since comminuted cases tend to lie in varus, this requires extra care. Medical displacement of the shaft, bringing it into apposition with the head, will also facilitate this.

4. The four-part fracture presents special problems. In reducing it, the head should be held in place manually, against the proximal shaft and the appliance, while the screws are inserted. Adequate impaction of the head against the proximal shaft and the medial surface of the appliance should

UNITED STATES PATENT AND TRADEMARK OFFICE
CERTIFICATE OF CORRECTION

PATENT NO. : 4,503,847

DATED : March 12, 1985

INVENTOR(S) : WILLIAM H. MOURADIAN

It is certified that error appears in the above–identified patent and that said Letters Patent are hereby corrected as shown below:

occur, thus restoring the medial buttress. Occasionally, with significant loss of substance or with a thin head fragment this may be especially difficult to accomplish. Indeed, this may result in excessive medial displacement of the shaft. This problem can be minimized by contouring the rod proximally to slightly reduce its radius of curvature. This will result in a more anatomic configuration.

5. Unusual humeral canal geometry may present difficulty. In this case the contour of the canal may guide the rod into a significantly improper degree of

UNITED STATES PATENT AND TRADEMARK OFFICE
CERTIFICATE OF CORRECTION

PATENT NO. : 4,503,847
DATED : March 12, 1985
INVENTOR(S) : WILLIAM H. MOURADIAN It is certified that error appears in the above-identified patent and that said Letters Patent are hereby corrected as shown below:

retroversion. The twist in the rod may be contoured to correct this. Also, the smaller rod size may be used and contoured to provide adequate three point distal fixation.

6. The role of intensive rehabilitation in producing a satisfactory clinical result cannot be over emphasized.--

Signed and Sealed this

Twenty-fourth Day of September 1985

[SEAL]

Attest:

DONALD J. QUIGG

Attesting Officer   Commissioner of Patents and Trademarks—Designate